(12) United States Patent
Bharadwaj et al.

(10) Patent No.: US 9,211,421 B2
(45) Date of Patent: Dec. 15, 2015

(54) INFANT WARMING ASSEMBLY WITH RADIANT HEATER AND HEATER SURFACE TEMPERATURE SENSOR

(75) Inventors: Sanjay Bharadwaj, Bangalore (IN); Uttama Kumar Sahu, Bangalore (IN); Sudip Saha, Bangalore (IN)

(73) Assignee: Koninklijke Philips N.V., Eindhoven (NL)

( * ) Notice: Subject to any disclaimer, the term of this patent is extended or adjusted under 35 U.S.C. 154(b) by 185 days.

(21) Appl. No.: 13/976,059

(22) PCT Filed: Jan. 2, 2012

(86) PCT No.: PCT/IB2012/050009
§ 371 (c)(1),
(2), (4) Date: Jun. 26, 2013

(87) PCT Pub. No.: WO2012/093347
PCT Pub. Date: Jul. 12, 2012

(65) Prior Publication Data
US 2013/0289677 A1   Oct. 31, 2013

Related U.S. Application Data

(60) Provisional application No. 61/430,571, filed on Jan. 7, 2011.

(51) Int. Cl.
*A61N 5/06* (2006.01)
*A61G 11/00* (2006.01)

(52) U.S. Cl.
CPC .............. *A61N 5/0625* (2013.01); *A61G 11/00* (2013.01); *A61G 2203/46* (2013.01); *A61N 2005/0636* (2013.01)

(58) Field of Classification Search
CPC ................... A61N 5/0625; A61N 2005/0636; A61G 11/00; A61G 2203/46; A61M 2005/3368; H05B 3/84; H05B 3/74; H05B 3/746; H05B 2213/07; H05B 2213/04; H05B 1/0283; H05B 1/02; H05B 1/0275; H05B 6/6452; H05B 6/6482; F24C 7/08; F24C 7/087; G05D 23/24
USPC .................. 165/200; 219/110, 446.1, 448.11, 219/448.12, 489–490
See application file for complete search history.

(56) References Cited

U.S. PATENT DOCUMENTS 3,920,000 A   11/1975   Atherton et al.
5,119,467 A   6/1992   Barsky et al.
(Continued)

FOREIGN PATENT DOCUMENTS

EP   711537 A1   5/1996
EP   753983 A2   1/1997
(Continued)

*Primary Examiner* — Navin Natnithithadha
*Assistant Examiner* — Kaylee Wilson

(57) ABSTRACT

An infant warming assembly includes a heater assembly having a heater surface temperature sensor, a skin temperature sensor, and a user interface to input a commanded skin temperature value. The skin temperature sensor and the commanded skin temperature value are used in controlling a temperature component of a control loop. The heater surface temperature sensor is used in controlling a power component of the control loop that powers the heater based at least in part upon the heater surface temperature sensor and a control signal from the temperature component.

2 Claims, 4 Drawing Sheets

(56) References Cited

U.S. PATENT DOCUMENTS

| | | | |
|---|---|---|---|
| 5,707,006 | A | 1/1998 | Skulic |
| 6,245,010 | B1 | 6/2001 | Jones |
| 6,443,885 | B1 | 9/2002 | Schuler |
| 6,464,627 | B1 | 10/2002 | Falk |
| 7,530,942 | B1 | 5/2009 | Diab |
| 2002/0091297 | A1 | 7/2002 | Falk |
| 2002/0161276 | A1* | 10/2002 | Mountain ................. 600/22 |
| 2003/0060818 | A1 | 3/2003 | Kannenberg |
| 2003/0197003 | A1 | 10/2003 | Kneuer |
| 2004/0062288 | A1 | 4/2004 | Falk |
| 2005/0008031 | A1 | 1/2005 | Tat et al. |
| 2005/0080316 | A1 | 4/2005 | Severns |
| 2007/0135675 | A1 | 6/2007 | MacKin et al. |
| 2009/0177257 | A1 | 7/2009 | Khodak et al. |
| 2010/0023098 | A1 | 1/2010 | Li et al. |
| 2010/0081859 | A1 | 4/2010 | Matsubara et al. |

FOREIGN PATENT DOCUMENTS

| | | |
|---|---|---|
| EP | 790050 A2 | 8/1997 |
| EP | 811363 A2 | 12/1997 |
| EP | 968698 A2 | 6/1999 |
| EP | 1060727 A1 | 12/2000 |
| EP | 1124169 A2 | 8/2001 |
| EP | 1124403 A2 | 8/2001 |
| EP | 1520572 A2 | 4/2005 |
| FR | 2891136 A1 | 3/2007 |
| GB | 929665 A | 6/1963 |
| WO | 9848757 A1 | 11/1998 |
| WO | 0180804 A1 | 11/2001 |
| WO | 02084425 A1 | 10/2002 |
| WO | 2009073355 A1 | 6/2009 |
| WO | 2010054457 A1 | 5/2010 |

* cited by examiner

INFANT WARMING ASSEMBLY WITH RADIANT HEATER AND HEATER SURFACE TEMPERATURE SENSOR

The disclosed and claimed concept relates generally to an infant warming assembly and, more particularly, to an infant warming assembly that employs a radiant heater having a heater surface temperature sensor that can be used at least in part to command power delivered to the heater.

Infant warmers are generally known in the relevant art. Infant warmers typically are employed in hospital or other medical settings to warm an infant in order to compensate for heat that is lost by a newborn through convection and radiation. The ability for a newborn infant to maintain and regulate its body temperature is very important for survival and growth. Infants who are born prematurely or at a low birth weight or who require medical procedures that require them to remain unclothed can struggle to maintain body temperature. Calories that are expended in maintaining body temperature cannot be otherwise utilized to help the infant's weight gain, which is undesirable. It has thus been known to provide infant warmers that provide heat to an infant predominantly through radiation in the medium wave infrared spectrum.

Known infant warmers have typically employed the difference between a commanded skin temperature and a measured skin temperature to manipulate heater power. While such architecture has been generally effective for its intended purposes, it has not been without limitation due to variations in supply voltage to the radiant heater, variations in heater characteristics between samples and with age, variations in ambient conditions, and slow heater response to changes in input power. It thus would be desirable to provide an improved infant warming assembly that provides improved performance.

Accordingly, an improved infant warming assembly includes a radiant heater control apparatus that controls a heater assembly having a heater surface temperature sensor that measures a surface temperature of a heater element. The radiant heater control apparatus further includes a skin temperature sensor and a user interface that can be used to input a commanded skin temperature value. The skin temperature sensor and the commanded skin temperature value are used in controlling a temperature component of a control loop. The heater surface temperature sensor is used in controlling a power component of the control loop that powers the heater based at least in part upon the heater surface temperature sensor and a control signal from the temperature component.

According, an aspect of the disclosed and claimed concept is to provide an improved infant warming assembly.

Another aspect of the disclosed and claimed concept is to provide an improved radiant heater control apparatus of an infant warming assembly.

Another aspect of the disclosed and claimed concept is to provide an improved radiant heater control apparatus having a control loop that includes a temperature component and a power component, with the power component being driven at least in part by a heater surface temperature sensor and a control signal from the temperature component that is based at least in part upon a skin temperature sensor and a commanded skin temperature value.

These and other aspects of the disclosed and claimed concept are provided by an improved radiant heater apparatus structured for use in an infant warming assembly. The general nature of the radiant heater apparatus can be stated as including a radiant heater and a radiant heater control apparatus. The radiant heater comprises a heater element and a heater surface temperature sensor disposed on the heater element, the heater surface temperature sensor being structured to sense a current heater surface temperature. The radiant heater control apparatus comprises a processor apparatus and a control loop. The processor apparatus has a number of routines executed thereon that comprise a user interface routine which enables the setting of a commanded skin temperature value. The control loop comprises a temperature component and a power component. The temperature component comprises a skin temperature sensor, a bed temperature controller, and a heater surface temperature lookup, the skin temperature sensor being structured to sense a current skin temperature, the bed temperature controller being structured to generate a bed temperature control signal based at least in part upon the commanded skin temperature value and the current skin temperature, the heater surface temperature lookup being structured to generate a commanded heater surface temperature value based at least in part upon the commanded skin temperature value, the temperature component being structured to generate a heater surface temperature control signal based at least in part upon the bed temperature control signal and the commanded heater surface temperature value. The power component comprises a heater power controller and a heater power lookup, the heater power controller being structured to generate a heater power control signal that is based at least in part upon the heater surface temperature control signal and the current heater surface temperature, the heater power lookup being structured to generate a commanded heater power value that is based at least in part upon the commanded skin temperature value. The radiant heater is structured to be powered based at least in part upon the heater power control signal and the commanded heater power value.

A further understanding of the disclosed and claimed concept can be gained from the following Detailed Description of Exemplary Embodiments when read in conjunction with the accompanying drawings in which:

Similar numerals refer to similar parts throughout the specification.

Figure 1:
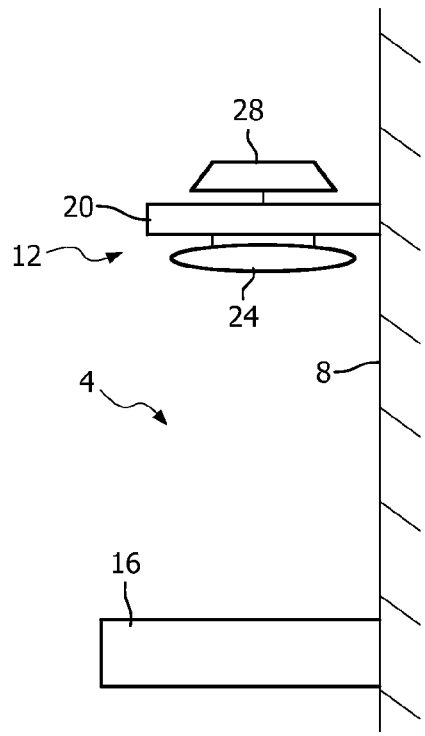
FIG. 1 is a schematic depiction of an improved infant warming assembly in accordance with the disclosed and claimed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

An improved infant warming assembly 4 in accordance with an embodiment of the disclosed and claimed concept is depicted generally in FIG. 1. Infant warming assembly 4 is depicted in FIG. 1 as being mounted to a wall 8, although in other embodiments it is understood that infant warming assembly 4 could be configured to be free-standing or otherwise situated without departing from the present concept. Infant warming assembly 4 is depicted as including a radiant heater apparatus 12 and a bed 16, both of which are mounted to wall 8, but as mentioned above, could be otherwise situated without departing from the present concept.

As can further be seen from FIG. 1, the exemplary embodiment of radiant heater apparatus 12 includes a frame 20 connected with wall 8, and further includes a heater assembly 24 and a reflector 28 disposed on frame 20. Heater assembly 24 includes a radiant heater 32 and a radiant heater control apparatus 36, and reflector 28 is provided in order to reflect the radiant energy generated by radiant heater 32 toward bed 16.

Radiant heater 32 can be said to include a heater element 40 and a heater surface temperature sensor 44, with heater surface temperature sensor 44 being configured to sense a surface temperature of heater element 40. In the exemplary embodiment depicted herein, heater element 40 is a ceramic heating element having an electrical resistance wire about which ceramic material is cured in situ. More particularly, the ceramic material can be poured about both the electrical resistance wire and heater surface temperature sensor 44 which, in the embodiment depicted herein, is a thermocouple. While other types of radiant heater elements can be employed without departing from the present concept, a ceramic heating element is well suited to the addition of heater surface temperature sensor 44 because such ceramic material can be readily poured into a mold, for instance, to embed the resistance wire and heater surface temperature sensor 44 therein.

Figure 2:
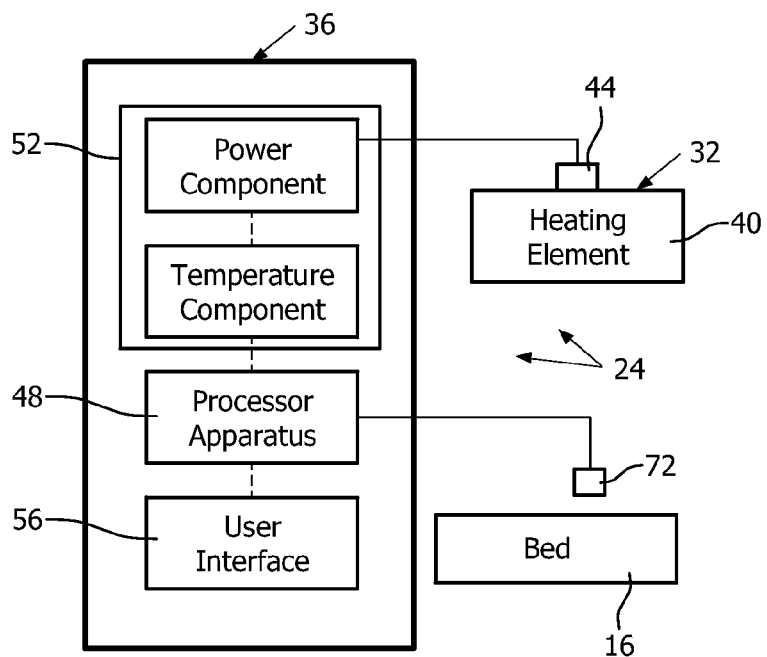
FIG. 2 is another schematic depiction of the infant warming assembly of FIG. 1.

Radiant heater control apparatus 36 is schematically depicted in FIG. 2 as including a processor apparatus 48, a control loop 52, and a user interface 56 by which a user such as a nurse, technician, or other individual can input a commanded skin temperature value 60. As will be discussed in greater detail below, user interface 56 is in the form of a routine that is executable on processor apparatus 48 and that can include an output apparatus such as a visual display screen and an input apparatus such as a keypad and/or a touch sensitive component of a touch sensitive display, by way of example, connected with processor apparatus 48. As will be set forth elsewhere herein, other routines are executable on processor apparatus 48 to perform other functions on radiant heater apparatus 12.

Figure 3:
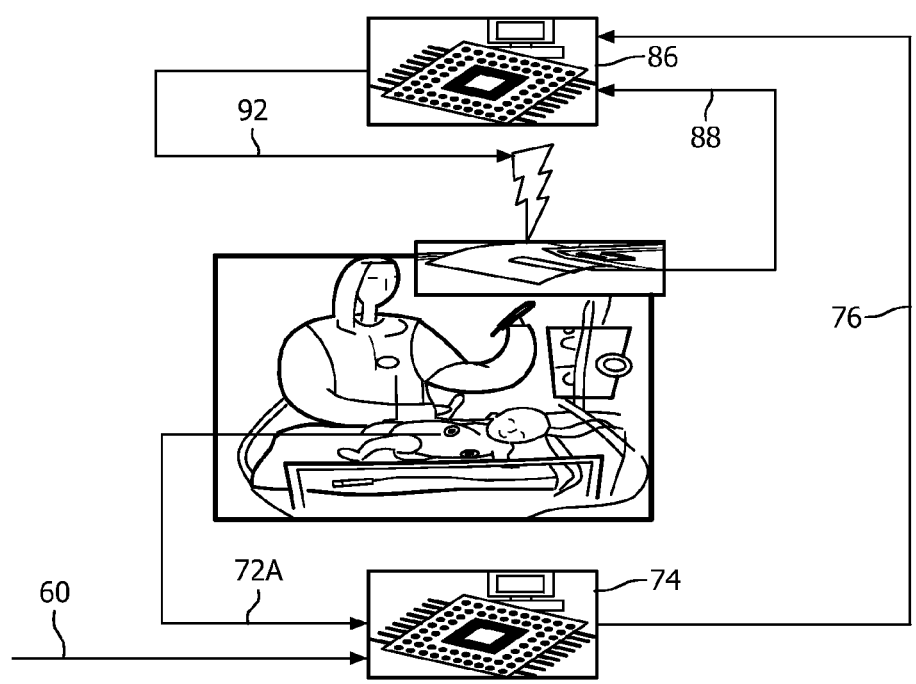
FIG. 3 is a diagrammatic depiction of a radiant heater control apparatus of the infant warming assembly of FIG. 1.

As can be understood from FIGS. 2 and 3, control loop 52 includes a temperature component 64 and a power component 68. In general terms, temperature component 64 employs as inputs commanded skin temperature value 60 and a signal from a skin temperature sensor 72 that is connected with the skin of the patient. In the exemplary embodiment depicted herein, skin temperature sensor 72 is a thermistor. Output from temperature component 64 is provided to power component 68 which further employs as an input signal from heater surface temperature sensor 44. Again in general terms, power component 68 is in the nature of a power control loop that controls power to radiant heater 32 based upon a surface temperature of heater element 40, as generated by heater surface temperature sensor 44, and by signals from temperature component 64 that are based at least in part on a difference between commanded skin temperature value 60 and a current skin temperature signal 72A generated by skin temperature sensor 72.

Figure 4:
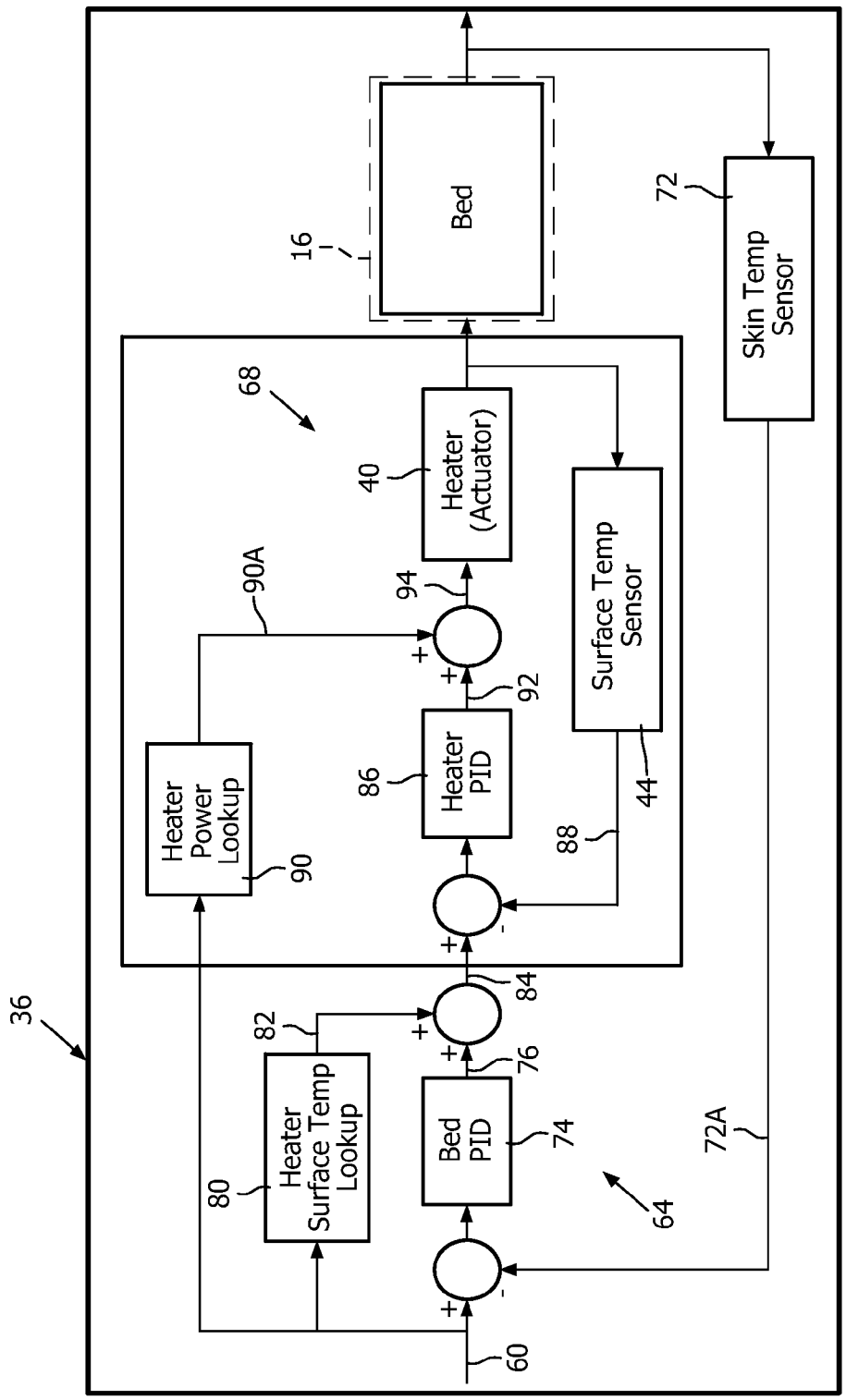
FIG. 4 is a flow diagram of the radiant heater control apparatus of FIG. 3.

More particularly, and as can be understood from FIG. 4, temperature component 64 can be said to include skin temperature sensor 72 and a bed temperature controller 74. In the exemplary embodiment depicted herein, bed temperature controller 74 is a Proportional/Integral/Derivative (PID) controller, and thus bed temperature controller 74 can also be referred to herein as bed PID 74. The difference between commanded skin temperature value 60 and current skin temperature signal 72A from skin temperature sensor 72 is input to bed temperature controller 74. Bed temperature controller 74 then generates a bed temperature control signal 76 that is based at least in part upon commanded skin temperature value 60 and current skin temperature signal 72A.

Temperature component 64 can further be said to include a heater surface temperature lookup 80 which employs one or more tables and/or one or more algorithms to derive or otherwise generate the heater surface temperature that would be nominally needed in order to achieve commanded skin temperature value 60 on the patient. In the exemplary embodiment described herein, the relationship between heater surface temperature and skin temperature is derived from data obtained via experimentation. More particularly, a set of heater surface temperature values and resultant skin temperature values are input into a computer program which fits the data to a nonlinear curve that employs a polynomial relation. The curve may be in the form of a mathematical function which, responsive to an input such as commanded skin surface temperature 60, outputs a corresponding heater surface temperature value. Once the mathematical function is derived for heater 40 which has known physical dimensions and is situated at a known distance from the patient, the function can be employed in the logic of heater surface temperature lookup 80 to employ commanded skin temperature value 60 to generate a heater surface temperature value.

Such a heater surface temperature value is communicated as a commanded heater surface temperature signal 82, and this is combined with bed temperature signal 76 to form a heater surface temperature control signal 84 that is input to power component 68. In this regard, it is noted that a nominal commanded heater surface temperature might be on the order of, say, 250° C., whereas the difference between commanded skin temperature value 60 and current skin temperature value 72A might be two orders of magnitude less and might be no more than a degree Centigrade or a fraction thereof. In order for bed temperature control signal 76 to be meaningfully combined with commanded heater surface temperature signal 82, bed temperature controller 74 scales up its output by, for example, an entire order of magnitude, although greater and lesser amounts of scaling up can be provided depending upon the needs of the system. It is also understood that other methodologies may be employed to combine bed temperature control signal 76 and commanded heater surface temperature signal 82 in a fashion that will enable bed temperature control signal 72 to be meaningfully combined with commanded heater surface temperature signal 82.

As can further be understood from FIG. 4, power component 68 can be said to include a heater power controller 86 and a heater power lookup 90. Heater power controller 86 is in the exemplary form of a PID controller, and heater power controller 86 thus can be referred to herein as heater PID 86.

Heater surface temperature control signal 84 and a current heater surface temperature signal 88 from heater surface temperature sensor 44 are combined and are input to heater power controller 86. Heater power controller 86 thus generates a heater power control signal 92 that is based at least in part upon heater surface temperature control signal 84 and current heater surface temperature signal 88. In this regard, heater power controller 86 may employ some conversion logic or scaling to convert the temperature-based inputs, i.e., heater surface temperature control signal 84 and current heater surface temperature signal 88, into a power-based output, i.e., heater power control signal 92.

Heater power lookup 90 includes one or more lookup tables and/or one or more algorithms to derive or otherwise generate a heater power lookup signal 90A that is based at least in part upon commanded skin temperature value 60 and can be generally characterized as the nominal heater power that would be required in order to result in the patient having commanded skin temperature value 60. Heater power lookup signal 90A and heater power control signal 92 are combined into a commanded heater power value 94 that is used to control an actuator of heater element 40. Heater element 40 thus is operated according to commanded heater power value 94 to deliver radiant heat to bed 16. It is noted that bed 16 is indicated in dashed lines in FIG. 4 to indicate its conceptual presence but that to indicate that bed 16 is itself not a component of radiant heater control apparatus 36.

It thus can be seen that power component 68 is a separate control loop that directly controls heater power based upon a current surface temperature of heater element 40. By basing heater power upon the surface temperature of heater element 40 rather than merely upon current skin temperature signal 72A and/or commanded skin temperature value 60, heater power can be more accurately controlled and can respond more rapidly to conditions. For instance, heater element 40 could be over-driven in a transient fashion by providing more power than would typically be required at steady state to achieve commanded skin temperature value 60 since power component 68 would be controlling power to heater element 40 based upon a desired surface temperature of heater element 40 rather than a desired skin surface temperature. Such control architecture can provide more rapid responses that are not dependent upon input voltages and that are independent of variations among samples of heaters and do not vary with age of heater element 40.

That is, since the surface temperature of heater 40 is monitored and controlled with power component 68, it can be seen that the actual voltage of the power input that drives heater 40 is largely irrelevant as long as it is sufficient to drive heater 40 to operate according to commanded heater power value 94. Moreover, the performance of heater 40 can vary from sample to sample and can also degrade with age. Such variation among samples is largely irrelevant because the surface temperature of heater 40 is monitored and controlled. Moreover, degradation of performance of heater 40 with age is likewise largely irrelevant since the monitoring and control of the resultant surface temperature of heater 40 causes it to be operated at whatever duty cycle is needed in order to achieve the desired skin temperature in accordance with the control parameters set forth herein. Additionally, when heater 40 is replaced at the end of its lifespan with a similar replacement heater 40, control of replacement heater 40 can be achieved immediately without the need for software modifications or recalibration since its surface temperature is monitored and controlled as set forth above.

Figure 5:
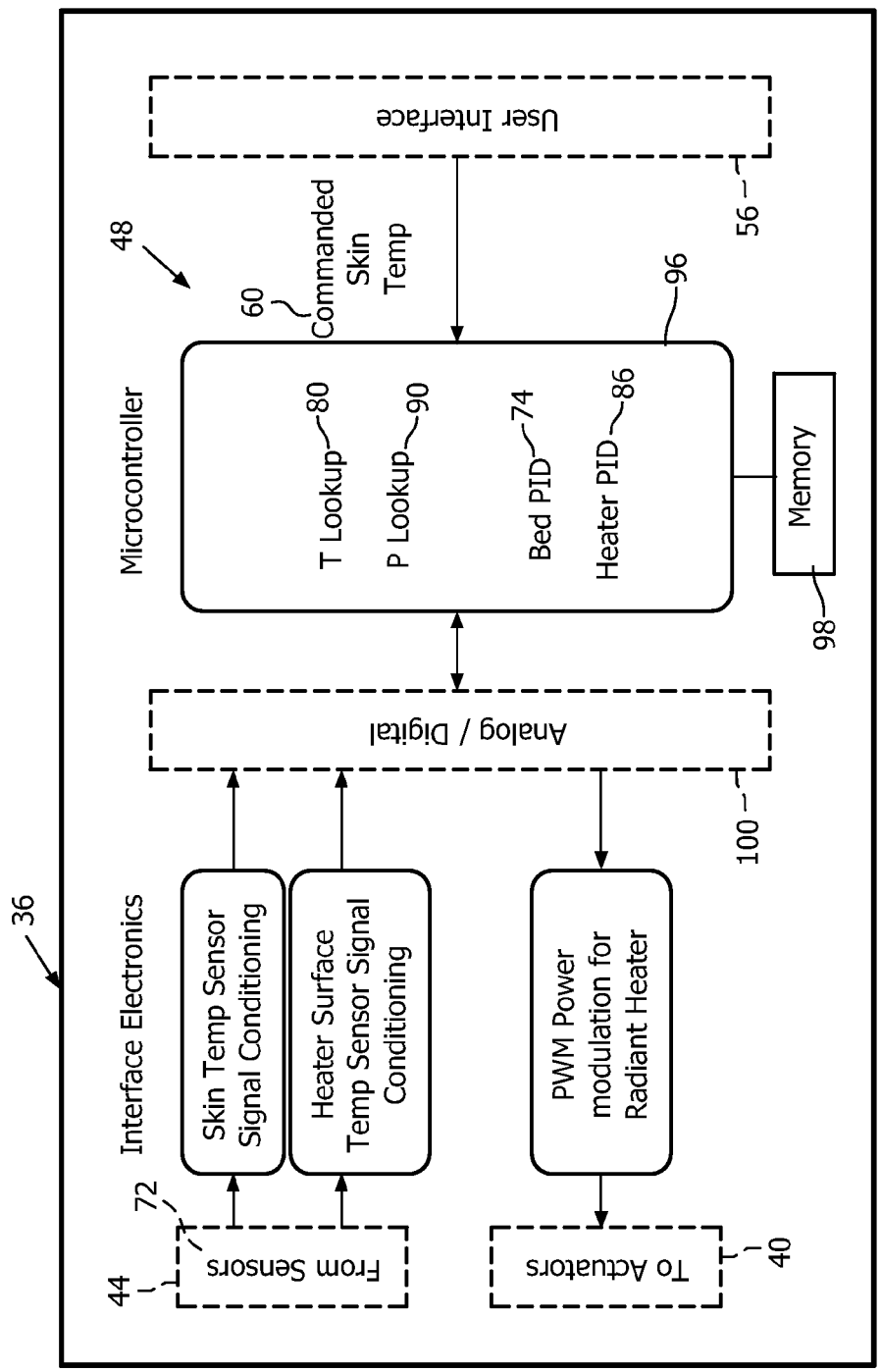
FIG. 5 is a diagrammatic depiction of the radiant heater control apparatus of FIG. 4.

As can be understood from FIG. 5, processor apparatus 48 includes a microcontroller 96 in communication with a memory 98. Microcontroller 96 can be any of a wide variety of processors such as microprocessors, microcontrollers, and the like without limitation. Memory 98 functions as an electronic storage that interfaces with microcontroller 96 and that can be in the form of any one or more of RAM, ROM, FLASH, and the like without limitation. As is generally understood, routines that are executed on microcontroller 96 are typically stored, at least in part, in memory 98 for retrieval and execution on microcontroller 96. In this regard, it is reiterated that user interface 56 is in the form of a routine that is executed on microcontroller 96. As can be understood from FIG. 5, other functions mentioned above are likewise in the form of routines that are executed on microcontroller 96. For instance, heater surface temperature lookup 80, heater power lookup 90, bed temperature controller 74, and heater power controller 86 are all implemented as software embedded in whole or in part on microcontroller 96 and/or memory 98. It is understood, however, that such routines can also be implemented on separate processors in a distributed arrangement without departing from the present concept.

Radiant heater control apparatus 36 can further be said to comprise a set of analog/digital conversion electronics 100 that can include one or more digital-to-analog converters (DACs) and analog-to-digital converters (ADCs) and other such electronics without departing from the present concept. It is also understood that analog/digital conversion electronics 100 can be implemented, in whole or in part, on microcontroller 96.

As can further be understood from FIG. 5, radiant heater control apparatus 36 can optionally include electronics that perform skin temperature signal conditioning and/or heater surface temperature sensor signal conditioning, as may be needed, although such signal conditioning potentially could be implemented in electronics that are provided with skin temperature sensor 72 and heater surface temperature sensor 44, respectively, or can be otherwise implemented in radiant heater control apparatus 36. Similarly, Pulse Width Modulation (PWM) typically will be employed to convert commanded heater power value 94 into a powered input for an actuator of heater element 40. In particular, heater element 40 typically will be ON/OFF in nature, and Pulse Width Modulation can be provided to rapidly switch heater element 40 between ON and OFF conditions where the "width" of the pulse refers to time. Such rapid switching of the duty cycle of heater element 40 typically will be provided by an optically-coupled thyristor switch driven by a NIDAQ card in order to achieve the high speed switching needed to accurately maintain the desired surface temperature of heater element 40. When commanded heater power value 94 is "increased", such as when the surface temperature of heater 40 needs to be raised, the "width" of the ON portion of the pulse may be increased or the OFF portion of the pulse may be decreased, or both. As such, the actual physical performance of heater 40 is largely irrelevant since commanded heater power value 94 is manipulated as set forth herein until the desired surface temperature of heater and the resultant desired skin temperature of the patient are achieved.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A radiant heater apparatus structured for use in an infant warming assembly, the radiant heater apparatus comprising:
    a radiant heater comprising a heater element and a heater surface temperature sensor disposed on the heater element, the heater surface temperature sensor being structured to sense a current heater surface temperature;
    a radiant heater control apparatus that comprises a processor apparatus and a control loop;
        the processor apparatus having a number of routines executed thereon that comprise a user interface routine which enables the setting of a commanded skin temperature value;
        the control loop comprising a temperature component and a power component;
            the temperature component comprising a skin temperature sensor, a bed temperature controller, and a heater surface temperature lookup, the skin temperature sensor being structured to sense a current skin temperature, the bed temperature controller being structured to generate a bed temperature control signal based at least in part upon the commanded skin temperature value and the current skin temperature, the heater surface temperature lookup being structured to generate a commanded heater surface temperature value based at least in part upon the commanded skin temperature value, the temperature component being structured to generate a heater surface temperature control signal based at least in part upon the bed temperature control signal and the commanded heater surface temperature value;
            the power component comprising a heater power controller and a heater power lookup, the heater power controller being structured to generate a heater power control signal that is based at least in part upon the heater surface temperature control signal and the current heater surface temperature, the heater power lookup being structured to generate a commanded heater power value that is based at least in part upon the commanded skin temperature value; and
    the radiant heater being structured to be powered based at least in part upon the heater power control signal and the commanded heater power value.

2. An infant warming assembly employing the radiant heater apparatus of claim 1.

* * * * *